United States Patent [19]

Nordlund

[11] Patent Number: 5,134,064
[45] Date of Patent: Jul. 28, 1992

[54] METHOD FOR THE DETERMINATION OF MICROBE CONCENTRATIONS BY MEANS OF A PLATING METHOD

[75] Inventor: Viljo Tapio J. Nordlund, Helsinki, Finland

[73] Assignee: Valio Meijerien Keskusosuusliike, Helsinki, Finland

[21] Appl. No.: 630,783

[22] Filed: Dec. 21, 1990

Related U.S. Application Data

[63] Continuation of Ser. No. 17,546, Feb. 24, 1987, abandoned.

[30] Foreign Application Priority Data

Feb. 21, 1986 [FI] Finland .................................. 860767

[51] Int. Cl.$^5$ .......................... C12Q 1/06; C12Q 1/24; C12M 1/16
[52] U.S. Cl. .......................................... 435/39; 435/30; 435/34; 435/29; 435/297; 435/299; 435/300; 435/301
[58] Field of Search ..................... 435/30, 34, 39, 297, 435/299, 300, 301, 29; 436/165

[56] References Cited

U.S. PATENT DOCUMENTS

| | | | |
|---|---|---|---|
| 3,729,382 | 12/1970 | Shaffer et al. | 195/139 |
| 3,787,290 | 1/1974 | Kaye | 195/103.5 R |
| 3,892,632 | 7/1975 | Campbell et al. | 195/103.5 R |
| 3,928,136 | 12/1975 | Launey | 195/54 |
| 4,054,490 | 10/1977 | Vesterberg | 195/103.5 K |
| 4,204,045 | 5/1980 | Kjellender et al. | 435/301 |

FOREIGN PATENT DOCUMENTS

| | | | |
|---|---|---|---|
| 1154614 | 10/1983 | Canada | 73/178 |
| 2351617 | 4/1975 | Fed. Rep. of Germany . | |
| 2117074 | 7/1972 | France . | |
| 2204689 | 5/1974 | France . | |
| 901889 | 7/1962 | United Kingdom . | |
| 1314296 | 4/1973 | United Kingdom . | |
| 1437404 | 5/1976 | United Kingdom . | |
| 1478575 | 7/1977 | United Kingdom . | |

OTHER PUBLICATIONS

Thomson, Donnelly & Black 1960 A Plate Loop Method for Determining Viable Counts of Raw Milk, J. Milk Food Technol. 26: 156 to 171 cited in the Specification.

FIL-IDF 100:1981 Liquid Milk Enumeration of Microorganisms Colony Count Technique at 30 C. cited in the Specification p. 11. Corresponding to ISO/DP 6610.

*Standard Methods for the Examination of Dairy Products*, pp. 77–93; 315–317 (E. H. Marth ed. 14th ed. 1978).

Labinskaya, A. S. *Microbiology and Technical Means For Carrying Out Microbiological Studies*, Medicine Publishers, Moscow, pp. 52–53 (1968).

Yegorov, N. S., *Antagonist Microbes and Biological Methods For the Determination of Antibiotic Activity*, Uysslaya Shkola Pub., Moscow, pp. 51–54 (1965).

*Primary Examiner*—Esther L. Kepplinger
*Assistant Examiner*—Toni R. Scheiner
*Attorney, Agent, or Firm*—Nixon & Vanderhye

[57] ABSTRACT

The invention relates to a method for the determination of microbe concentrations by means of a plating method, wherein a sample and a medium are plated in a dish, the medium is allowed to solidify and the solidified plate is incubated, wherein the colonies in the plate are counted. According to the method the microbes are inoculated to a medium solidifying in a dish and in such a manner that its layer thickness varies in a controlled manner. Also disclosed is a dish which is suitable for the determination of microbe concentrations by means of a plating method and the bottom part of which has such a shape that a solidified layer is formed in the dish after the plating of the sample and the medium, the thickness of the layer varying in a controlled manner.

12 Claims, 2 Drawing Sheets

METHOD FOR THE DETERMINATION OF MICROBE CONCENTRATIONS BY MEANS OF A PLATING METHOD

This is a continuation in part of application Ser. No. 07/017,546, filed Feb. 24, 1987, now abandoned.

FIELD OF THE INVENTION

The invention relates to a method for the determination of microbe concentrations by a plating method, wherein a sample and a medium are plated in a dish, the medium is allowed to solidify and the solidified plate is incubated, whereafter the colonies in the plate are counted. The invention is also concerned with a dish suitable for the determination of microbe concentrations by means of a plating method.

BACKGROUND OF THE INVENTION

In the dairying and other food stuff microbiology, medical microbiology as well as in general microbiology, determination of the number of microbes contained in a sample is generally carried out by means of dilution plate methods. Many of the so-called international comparative methods are of this type.

In dilution plate methods, a certain volume of a sample to be examined or of a dilution thereof is inoculated in a petri dish. E.g. 10 to 15 ml of a sterile culture medium capable of solidifying (agar) and having a temperature of $45° \pm 1°$ C. is poured on the sample. The sample is immediately mixed with the medium, and the solidification is allowed to take place at room temperature on a horizontal surface. The sample and the medium can also be mixed before the plating. The solidified medium forms a layer of even thickness on the dish. The solidified plates are turned upside down and placed in an incubator (incubation). The incubation temperatures (e.g. 10° C., 30° C., 37° C., 44° C., 55° C.) and the incubation time (e.g. 2, 3, 6 and 10 days) depend on the method applied, mainly on what microbe groups are to be examined. The dishes are in a horizontal position during the incubation.

After the incubation, colonies in the petri dish are counted. The amount of the inoculum in the sample and the dilution ratios being known, the number of microbes per one unit volume or one unit weight of the sample, usually microbes/ml or microbes/g, can be determined from the number of countable colonies.

The medium may contain as wide a diversity of nutrients as possible in order that as many microbe types of the sample as possible would have the required growth conditions (a so called total colony count). The nutrients of the medium may also be restricted or known growth inhibiting compounds may be added to the medium. Such media are referred to as selective media, and the object is to make a certain microbe group distinguishable.

The counting can be carried out ocularly (by means of known axialiary devices) or by means of various electrical counting devices (automatic colony counters).

A high colony concentration in the dish restricts the counting. It is customary to include in the counting only plates the colony quantity of which does not exceed a determined limit; for instance, with plates having a diameter of 9 cm, the upper limit is regarded to be 300 colonies. In order to be able to examine samples having a high microbe concentration, it is necessary to use dilution techniques. In practice, it is usually always necessary to use dilutions in the plating work. The preparation of successive dilutions covers 70 to 90 percent of the working time required for the whole plating stage (depending on the supposed need of dilution). Correspondingly, the material need is a multiple of the number of dilutions.

Prior dilution plate methods have thus a disadvantage that they require the preparation of large dilutions series and the cultivation of several dilutions. A great number of dishes is thereby required; further, a lot of incubation space is needed. In other words, the methods are complicated and time-consuming.

SUMMARY AND OBJECTS OF THE INVENTION

The object of the present invention is to provide the above disadvantages and enables a method which avoids the above disadvantages and enables the determination of microbe concentrations in a simple and reliable manner. This is achieved by means of the method according to the invention which is characterized in that the medium and the sample are mixed in order to obtain a homogeneous mixture and microbe concentration of which is constant, and the mixture is made to solidify so that the layer thickness of the medium varies in a controlled manner.

The basic idea of the invention is that a medium containing microbes is made to solidify in a dish so that the layer thickness of the solidified medium varies in a determined manner. The medium can be made to solidify in a single dish, so that the layer thickness is determined by means of the geometry of the dish. When the layer thickness of the medium varies from one dish portion to another, the quantity of the colonies varies correspondingly.

The basic idea can also be applied in such a manner that the mixture of the sample and the medium is metered in conventional petri dishes in amounts differing in an accurately determined way. This produces a series of plates having different layer thicknesses. The method as such, however, does not offer other rationalization advantages than the elimination of the need of successive dilutions.

According to the basic idea of the invention, developed colonies are distinguished after incubation in different densities at the enumeration stage, the density being at its lowest in the thinnest agar layers and at its highest in the thickest layers, varying with the geometry of the medium in areas having a layer thickness therebetween. When the sample and the medium (agar) are mixed carefully before plating, the amounts thereof being known and the geometry of the medium and the dish mathematically controlled, the microbe concentration of the sample is easy to determine. All information corresponding with accepted microbiological standards can be utilized in the determination: only colonies clearly distinguishable in the different layer thickness zones of the plate are taken into account. The layer thickness gradient determines the density gradient of the colonies, and this is taken into account in the mathematics of the colony enumeration. At the plating stage, it is of importance that the dishes are really positioned on a horizontal surface.

The advantages of the plating method according to the invention include:

1. No successive dilutions are necessary, because the colony density is sufficiently low to be counted at least in some parts of the plate by virtue of the varying layer thickness of the culture medium. As compared with prior methods, a 70 to 90 percent saving is obtained in the working time, because no successive dilutions are needed.

2. The saving obtained in the culture medium is proportional to the need of successive dilutions in prior methods (as well as, consequently, to the number of parallel dishes needed).

3. If disposable dishes are used, the material savings are proportional to the number of successive dilutions required in prior methods.

4. The need of incubation space is reduced considerably because no parallel dishes required by successive dilutions are needed. The same applies directly to the need of working rooms and material facilities.

5. It is not necessary to count the colonies over the whole dish, but a colony material sufficient for the determination is obtained from counting zones and sectors determined by the geometry of the bottom of the dish. The counting operation is also simplified and speeded by the fact that dilution and its consequences are eliminated.

6. The entire method, including the colony enumeration, can be mechanized and automated, mainly by utilizing and modifying prior techniques.

The microbe concentrations obtained by means of the method according to the invention correlate extremely well with results obtained by means of prior methods. The method can replace all prior dilution plate methods.

The invention is also concerned with a dish suitable for the determination of microbe concentrations by means of a plating method wherein a sample and a medium are plated, the medium is allowed to solidify, and the solidified plate is incubated, whereafter the colonies in the plate are counted. The dish is characterized in that the shape of the dish is such that after the plating of the sample and the medium, a solidified layer having a controlledly varying thickness is formed in the dish.

The basic idea of the invention, i.e. that the thickness of the solidified medium in the dish varies in a known, controllable manner, can be realized by the use of dishes of a new type: the dish is such in shape that after the mixture of a sample and a medium has been plated on a horizontal surface, a solidified layer is formed in the dish the thickness of which layer varies in a controlled manner. This new type of dish may be e.g. round, such as a conventional petri dish, or rectangular, for instance. The layer thickness of the medium is adjusted to a desired value by giving the bottom surface of a round dish a spherical or a mathematically controlled aspherical shape which may be rising or descending. The bottom of a round dish can also be made rising or descending by providing the dish with concentrically ring-shaped, horizontal planar surface areas, with a circular planar surface area in the middle. The bottom of a rectangular dish may rise linearly, along a circular arc or in some other mathematically controlled manner. It is also possible to provide the bottom of a rectangular dish with rectangular planar surface areas to make it rising. A preferred shape of a rectangular dish is a rectangle. The geometry of the dish can also be set by means of partitions of different heights positioned on the bottom thereof. The minimum layer thickness of the medium may be e.g. 1 mm and the maximum thickness 10 mm in the dishes according to the invention.

All the advantages offered by the method according to the invention can be achieved by means of this kind of dish. No successive dilutions are needed, and the savings obtained in the materials, in the medium and in the incubation space are considerable as compared with prior methods. When using a dish having the shape of a rectangle, the need of medium is automatically smaller, at best only about 50 percent of the medium need of a petri dish, and the need of incubation space is over 20 percent smaller than that of round dishes, calculated on the surface area.

Accordingly, it is most advantageous according to the invention to use a dish having the shape of a rectangle. Furthermore, it is thereby preferable that the sample (inoculum) and the used medium are mixed properly before plating.

DETAILED DESCRIPTION OF THE INVENTION

Figure 1A:
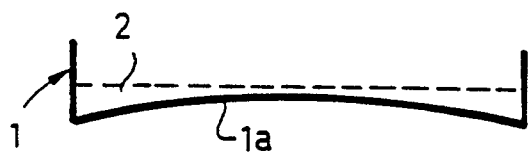
FIGS. 1A, 2A, 3, 4A, 5, 6 and 7 are vertical sectional views of the different embodiments of the dish according to the invention and the respective media.
Figure 1B:
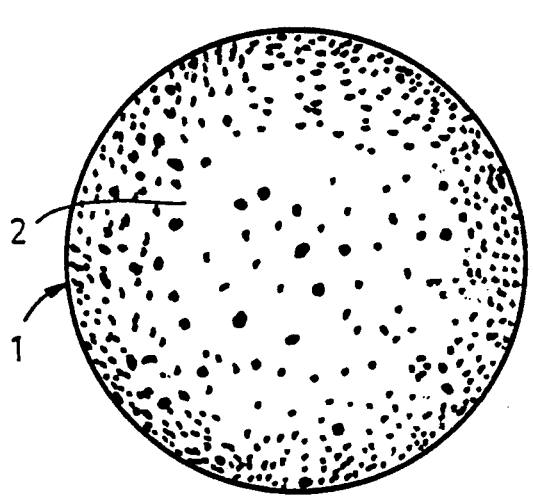
FIGS. 1B, 2B and 4B are top views of the respective dishes.

FIGS. 1A and 1B show a dish 1 which is round as seen from above and a bottom 1a of which is upwardly convex. The medium is designated by the reference numeral 2. It appears from the figures that when the layer thickness of the medium increased towards the outer periphery of the dish in a known manner determined by the geometry of the bottom of the dish, the colony density increases correspondingly.

Figure 2A:
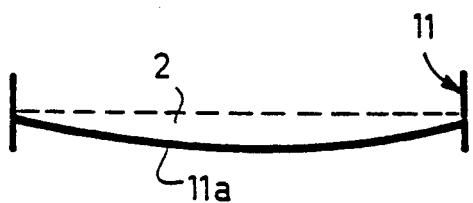
Figure 2B:
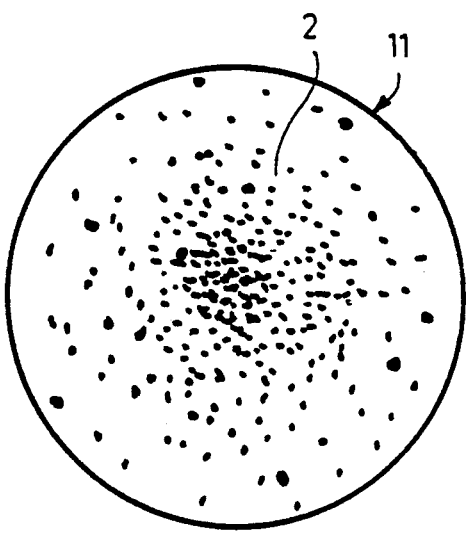

FIGS. 2A and 2B show a dish 11 which differs from the preceding one in that a bottom 11a thereof is downwardly convex, and, as a consequence, the layer thickness of the medium 2 and, correspondingly, the colony density is at its highest in the middle of the dish, decreasing towards the edges of the dish.

Figure 3:
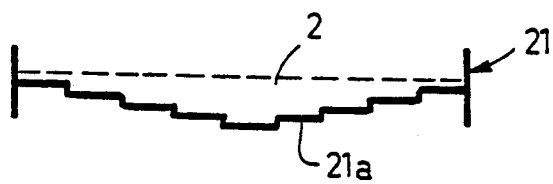

FIG. 3 shows a dish 21 a bottom 21a of which is formed by horizontal planar surface areas which are arranged concentrically so that the shape of the bottom changes in a stepwise manner. The dish is thus provided with circular layer thickness zones corresponding to the geometry of the bottom.

Figure 4A:
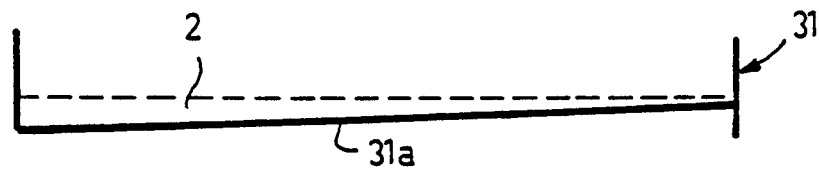
Figure 4B:
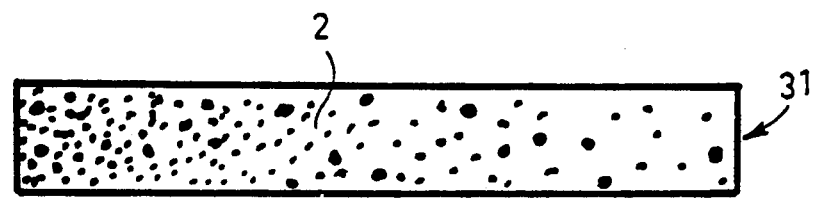

FIGS. 4A and 4B show a dish 31 which has the shape of a rectangle as seen from above and the shape of a bottom 31 of which changes linearly. The layer thickness increases from one short side of the dish towards the other, and the quantity of the colonies increases in a corresponding way.

Figure 5:
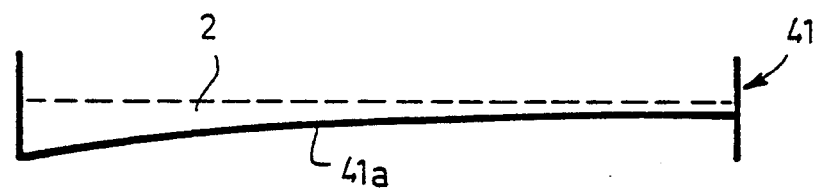

FIG. 5 shows a dish 41 a bottom 41a of which rises in an arched manner, the layer thickness gradient and the density gradient of the colonies changing accordingly.

Figure 6:
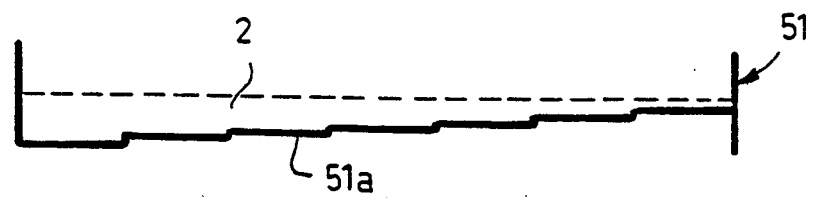

FIG. 6 shows a dish 51 a bottom 51a of which is formed by rectangular planar surface areas so that it rises in a stepwise manner. Layer thickness zones corresponding with the geometry of the bottom of the dish are thereby formed in the dish.

Figure 7:
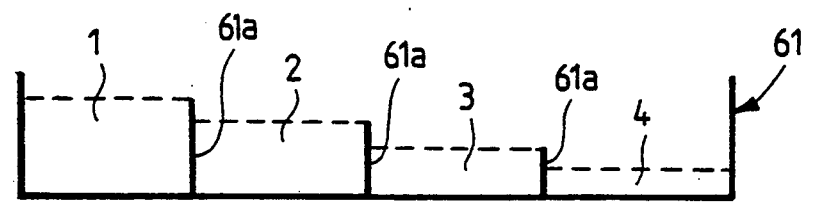

FIG. 7 shows a dish 61 the bottom of which is provided with partitions 61a. The sample-agar mixture is introduced into a compartment 1 wherefrom part of the mixture flows into a compartment 2, etc. so that separate layer thickness zones are formed.

The invention will be illustrated in more detail by means of the following examples.

EXAMPLE 1

1 µl of a milk sample is inoculated aseptically (a loop or a micropipette) in 12 ml of a molten sterile Standard Plate Count Agar (such as FIL-IDF 100:1981) contained in a sterile test tube and cooled to a temperature of 45° C. After the inoculation the mixture of the sample and agar is shaked properly e.g. in a test tube mixer.

After the mixing the sample-agar mixture is plated in a rectangular dish the bottom of which is rising, being formed by horizontal, rectangular planar surface areas. The dish comprises five planar surface areas, the size of each are being 4 cm². The planar surface areas are stepped with 2 mm height differences in a rising manner. A liquid amount of 12 ml, which is the agar volume of the example, fills the described dish in such a manner that five sectors equalling in surface area but having differing agar layer thicknesses are formed in the dish. The layer thicknesses are 2 mm in Sector I, 4 mm in Sector II, 6 mm in Sector III, 8 mm in Sector IV and 10 mm in Sector V; the agar amounts (and the sample amounts) being correspondingly: I 0.80 ml (0.066 µl), II 1.60 ml (0.133 µl), III 2.40 ml (0.199 µl), IV 3.20 ml (0.266, µl) and V 4.00 ml (0.333 µl). The total agar surface area of the sectors is 20 cm² after the plating. The agar and sample amounts of the sectors are also shown in Table 1.

The dish is closed with a lid and incubated in a horizontal position during 72±2 hours at a temperature of +30±1° C.

The results are calculated separately for each sector by dividing the number of the countable colonies in each sector (in practice <40 colonies per sector) by the sample amount specific for each sector; in the present example, the sample amount is 0.066 µl or 0.000066 ml in Sector I, and 0.333 µl or 0.000333 ml in Sector V. Accordingly, if the number of the colonies in Sector I is 3, there are 3 colonies per 0.000066 ml~45,000 colonies per ml; and if the number of the colonies in Sector V is 17, there are 17 colonies per 0.000333 ml~50,000 colonies per ml. The result gives directly the microbe quantity of the sample per ml. The numbers of the colonies in the sectors and the results calculated on the basis thereof are shown in Table 2.

The information obtained from all countable sectors can be utilized in the result by calculating the mean value of the results obtained from each sector.

TABLE 1

| Sector (A = 4 cm²) | Agar (ml) | Sample (ml) | % of the sample |
|---|---|---|---|
| V | 4.00 | 0.000333 | 33 |
| IV | 3.20 | 0.000266 | 28 |
| III | 2.40 | 0.000199 | 20 |
| II | 1.60 | 0.000133 | 13 |
| I | 0.80 | 0.000066 | 6 |

TABLE 2

| SPC × 1,000 | SPC-modification | | | | | the microbe quantity of the sample, microbes × 10³/ml | | | | |
|---|---|---|---|---|---|---|---|---|---|---|
| | I | II | III | IV | V | I | II | III | IV | V |
| 10 | 1 | 1 | 2 | 3 | 3 | — | — | — | 11 | 9 |
| 50 | 3 | 7 | 10 | 13 | 17 | 45 | 53 | 50 | 49 | 51 |
| 100 | 7 | 13 | 20 | 27 | 33 | 106 | 98 | 100 | 101 | 99 |
| 200 | 13 | 27 | 40 | 53 | 67 | 197 | 203 | 201 | 199 | — |

EXAMPLE 2

The sample is inoculated aseptically in agar in a dilution ratio of $10^{-4}$ (10 µl of the original sample to 100 ml agar). After the inoculation, the agar-sample mixture is mixed efficiently, and it is plated in conventional petri dishes in the amounts of 2, 5, 10, 20, 40 and 60 ml, so that the amounts of the original sample are 0.0002 ml, 0.0005 ml, 0.001 ml, 0.002 ml, 0.004 ml and 0.006 ml respectively. The dishes are incubated and the colonies are counted. The numbers of the colonies counted from the dishes are converted into the microbe density of the original sample by means of the following formula:

$$\text{the microbe density of the sample} = \frac{\text{the counted colony density}}{\text{the amount of the original sample}}$$

The results are shown in Table 3.

TABLE 3

| SPC × 1000 | Colonies in the dishes (amounts of sample-agar mixture) | | | | | |
|---|---|---|---|---|---|---|
| | 2 ml | 5 ml | 10 ml | 20 ml | 40 ml | 60 ml |
| 5 | 1 | 3 | 5 | 10 | 20 | 30 |
| 20 | 4 | 10 | 20 | 40 | 80 | 120 |
| 50 | 10 | 25 | 50 | 100 | 200 | 300 |
| 100 | 20 | 50 | 100 | 200 | (400) | (600) |
| 200 | (40) | (100) | 200 | (400) | — | — |
| 300 | (60) | (150) | 300 | — | — | — |
| 500 | (100) | (250) | (500) | — | — | — |

The parentheses in the table mean that it is not possible to count these colony densities in the dishes. When using petri dishes having a diameter of 90 mm, the bottom of the dish is completely covered with agar only in dishes containing 10 ml or more of agar.

References

Standard Plate Count Method:
1. FIL-IDF 100:1981 Liquid Milk Enumeration of Microorganisms Colony Count Technique at 30° C.
2. ISO/DP 6610 ibid.
3. APHA American Public Health Association Standard Methods for the Examination of Dairy Products 14th edition 1978, p. 77 to 93.

Plate Loop Method:
1. APHA 14th ed. p. 315 to 317.
2. Thompson, Donnelly & Black 1960 A Plate Loop Method for Determining Viable Counts of Raw Milk.
3. J. Milk Food Technol. 26: 156 to 171.

What is claimed is:

1. A pour plate method for determining microbe concentrations in a sample, said method comprising the steps of:
    (a) preparing a homogeneous mixture of a sample and a gelable liquid culture medium by distributing the microbe sample uniformly throughout the liquid culture medium so that the microbe concentration of the homogeneous mixture is constant;
    (b) pouring the homogeneous mixture of step (a) into a single dish wherein the dish is configured to permit the homogeneous mixture to solidify into regions of different layer thickness, the microbe concentration of which is constant throughout the mixture, and solidifying the mixture to provide a layer thickness gradient of the solidified homogeneous mixture in the dish;

(c) incubating the solidified homogeneous mixture to permit growth of microbe colonies; and, (d) counting microbe colonies in a selected region of the incubated solid mixture and determining the number of colonies therein based upon the volume of the region in which the colonies are counted, whereby the concentration of microbe in the mixture is constant throughout the incubated solidified mixture and the layer thickness determines colony number.

2. A method according to claim 1, wherein the homogeneous mixture of medium and sample is solidified in a plurality of dishes the layer thickness in each dish being controlled by metering in different volumes of the mixture.

3. The method of claim 1 in which the dish has a single compartment and provides a solidified layer having a controlled varying thickness.

4. The method of claim 3 in which the dish has a round cross-section.

5. The method of claim 3 in which the dish has a rectangular cross-section.

6. The method of claim 3 in which the dish has a concave bottom.

7. The method of claim 3 in which the dish has a convex bottom.

8. The method of claim 3 in which the dish has a bottom that is linearly rising.

9. The method of claim 3 in which the dish has a bottom that rises linearly along a circular arc.

10. The method of claim 3 in which the dish has series of concentrically ring-shaped horizontal planar surface areas with a circular planar area in the center.

11. The method of claim 3 in which the dish has series of concentrically-shaped rectangular planar surface areas.

12. The method of claim 1 in which the homogeneous mixture is solidified in a container for a predetermined volume of liquid, the container shaped to provide regions of different thickness of the solidified mixture to provide volumes that produce countable groups of microbe colonies.

* * * * *